United States Patent [19]
Hennig et al.

[11] 3,952,726
[45] Apr. 27, 1976

[54] MEDICAL DEVICE

[75] Inventors: Gerhard R. Hennig, Gauting; Klaus G. Hennig, Graben-Neufeld, both of Germany

[73] Assignee: Gerhard R. Hennig, Germany

[22] Filed: Dec. 4, 1974

[21] Appl. No.: 529,586

[30] Foreign Application Priority Data
Dec. 20, 1973   Germany............................ 2363563
Aug. 19, 1974   United Kingdom............... 36341/74

[52] U.S. Cl. .......................... 128/1 R; 128/DIG. 25; 128/283
[51] Int. Cl.² ....................................... A61B 19/00
[58] Field of Search............. 128/1 R, 283, DIG. 25; 3/1

[56] References Cited
UNITED STATES PATENTS
| | | | |
|---|---|---|---|
| 2,243,529 | 5/1941 | Grossman et al. | 128/1 R |
| 3,083,704 | 4/1963 | Swearingen | 128/1 R |
| 3,565,073 | 2/1971 | Giesy et al. | 128/283 |

Primary Examiner—Dalton L. Truluck

[57] ABSTRACT

A kit for closing the intestinal opening on an anus praeter patient, which comprises at least one permanent magnet adapted to be positioned in the region of the intestinal opening and magnetic means for closing the intestinal opening, said magnetic means being operable to be retained in the closed position by magnetic attraction to said permanent magnet and to be opened by manual separation of said magnetic means from said permanent magnet.

5 Claims, 5 Drawing Figures

MEDICAL DEVICE

The present invention relates to a kit for closing the intestinal opening on an anus praeter patient.

There are many colostomy and ileostomy patients who have an intestinal opening in their abdominal wall. The use of natural or artificial sphincters in such a location is impossible. The normal expedient is to close the opening by a special dressing or by wearing a waste bag.

The concept of this invention is to provide a reliable seal and/or to hold the waste bag by means of magnetic action. Accordingly, a permanent magnet, a magnet system, a soft magnetic material or a similar device is provided for fitting around the intestinal opening, while a matching counterpart made of permanent or soft magnetic material provides for the closing of this opening by magnetic action. The term "magnetic action" is to be understood to mean anything which is activated by magnetic forces, for instance attraction, repulsion or spreading of the respective parts in relation to the intestinal opening. The term "magnetic system" means a plurality of permanent magnets and/or soft magnetic material acting together. The term "soft magnetic material" means a material which is magnetizable or which becomes attracted by a magnet, but does not retain magnetism.

The kit, according to this invention, includes a ring-shaped permanent magnet, with radial, axial or multipole magnetization, to be implanted under the abdominal wall and fitted around the intestinal opening. The kit also includes a waste bag or sealing cap, the inlet of the waste bag and the sealing cap having a similar permanent or soft magnetic ring, or a matching magnetic system, incorporated therein. The respective magnets may be in one piece, composed of segments, etc.

Any known type of magnet can be employed to achieve the desired action.

The invention will be described further, by way of example, with reference to the accompanying drawing, in which.

Figure 1:
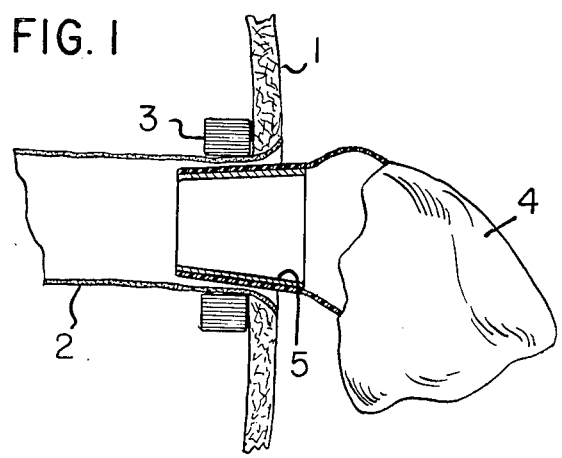
FIG. 1 is a diagrammatic cross-sectional side elevational view showing a preferred embodiment of the device of the invention appropriately fitted in place in a patient and with a waste bag inserted in position.
Figure 4:
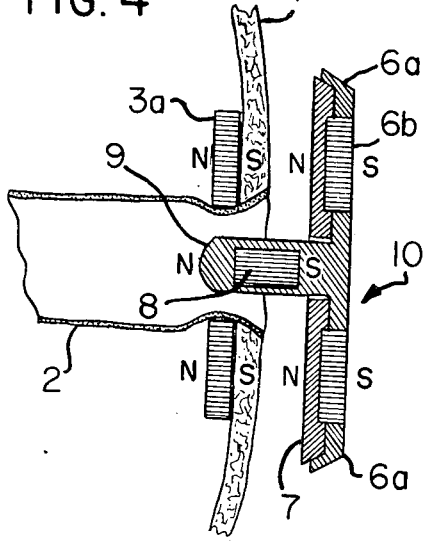
FIG. 4 is a view comparable with FIG. 1 but showing a slightly modified embodiment and with a sealing cap being put in place.

Referring first to FIGS. 1 and 4, implanted under abdominal wall 1 of a patient and around intestine 2 is a ring magnet 3. Waste bag 4 has an inlet 5 in the form of a soft magnetic or a permanent magnetic ring. The ring 5 is thus urged into ring 3, and is retained therein by magnetic action.

Figure 2:
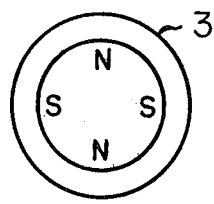
FIG. 2 is an elevational view illustrating diagrammatically the magnetization of the permanent magnet of the device of FIG. 1.
Figure 3:
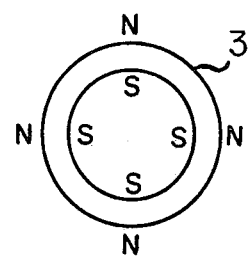
FIG. 3 is a view similar to FIG. 2 but illustrating an alternative way in which the magnet may be magnetized.

FIGS. 2 and 3 show alternative magnetizations for the implanted magnet 3. Other magnetizations are also possible, such as axial magnetization for the ring magnet 3 and its counterpart ring 5.

Figure 5:
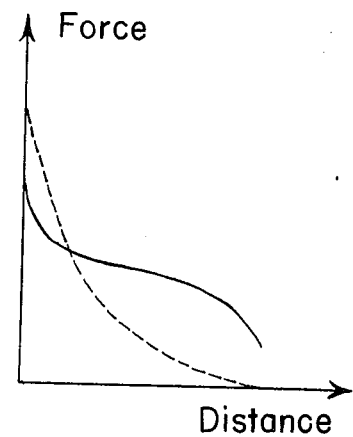
FIG. 5 is a graph illustrating the magnetic advantage obtained with the embodiment of FIG. 4.

It is possible to use a sealing cap instead of the waste bag. FIG. 4 shows a sealing cap 10 made of non-magnetic material, which has a disc-shaped portion 6a and a cylindrical portion 9 projecting therefrom. Ring magnet 6b, which is similar to the implanted ring magnet 3a, is located in disc-shaped portion 6, and core magnet 8 is located in cylinder 9. The center core magnet 8 increases the magnetic attraction between the implanted magnet 3a and the magnets 6b, 8 in the sealing cap 10 when spaced a wide distance (say, 10 to 20 mm) from magnet 3a, and reduces this magnetic attraction at a close distance (say, 3 to 7 mm). Thus, the force versus distance characteristic is improved. FIG. 5 shows this characteristic with the full line representing cap 10 with the center core magnet 8 and the dotted line representing cap 10 without magnet 8.

While core magnet 8 is shown in FIG. 4 as being permanently embedded in cylinder 9, it is apparent that the cap 10 can be provided with means (not shown) for axially adjusting the position of core magnet 8, e.g. towards or away from disc-shaped portion 6b. Suitable axial adjustment means include an adjusting screw for moving or tilting the core magnet 8 to the desired position or for sliding the magnet 8 towards or away from disc-shaped portion 6b.

When using a waste bag held by means of magnetic action, the magnet or the soft magnetic part of the bag may be made in a way that upon discarding the bag the magnet or the soft magnetic part can be used again.

In order to provide safe and non-skin irritating sealing both for the bag and the sealing cap, a suitable gasket 7, made for example out of moisture-adsorbing material and/or a soft resin, is advantageously placed between the bag or cap and the abdominal wall. This gasket 7 may contain medicaments of an antibiotic and/or scent suppressing and/or other nature.

In addition, before implantation, magnets 3 and 3a may be embedded in a material acceptable to human tissue, such as silicone, polyethylene, polyester and the like.

What is claimed is:

1. In combination, means for closing the intestinal opening on an anus praeter patient, which comprises an axially magnetized ring-shaped permanent magnet means comprising at least one permanent magnet, said ring-shaped permanent magnet means being adapted to be positioned around the intestinal opening and a magnetic sealing cap means for closing the intestinal opening, said sealing cap means including a cap member adapted to contact the abdominal wall of the patient and at least one ferromagnetic material arranged to be magnetically attracted to the ring-shaped magnet when the sealing cap means is in the closed position, said sealing cap means also including an axially magnetized permanent magnetic core member extending away from said ferromagnetic material in said sealing cap means and disposed to be inside the ring-shaped permanent magnet means when the sealing cap means is in the closed position, the magnetic core member being axially magnetized in such a way as to increase the magnetic attraction between the permanent magnet means and the ferromagnetic material of the sealing cap means when the distance between the ring-shaped permanent magnet means and the ferromagnetic material of the sealing cap means is greater than a predetermined value and to decrease said magnetic attraction when said distance is less than said predetermined value, said sealing cap means being operable to close said intestinal opening by magnetic attraction to said permanent magnet means and to be manually separable from said permanent magnet.

2. Means as claimed in claim 1, in which the ring-shaped permanent magnet means is enclosed in a material which is acceptable to human tissue.

3. Means as claimed in claim 1, in which the magnetic core member is located in the center of the sealing cap, so as to protrude through said ring-shaped permanent magnet.

4. Means as claimed in claim 1, in which the sealing cap means has a non-magnetic cylinder housing said magnetic core member, the position of said magnetic core member being adjustable in said cylinder.

5. A kit according to claim 1, in which the sealing cap member has a gasket made out of a soft, moisture-absorbing material.

* * * * *